United States Patent
Heys et al.

(10) Patent No.: US 9,802,220 B2
(45) Date of Patent: Oct. 31, 2017

(54) MOLYBDENUM (IV) AMIDE PRECURSORS AND USE THEREOF IN ATOMIC LAYER DEPOSITION

(75) Inventors: Peter Nicholas Heys, Crewe (GB); Rajesh Odedra, Victoria (CA); Sarah Louise Hindley, Liverpool (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/817,591

(22) PCT Filed: Aug. 25, 2011

(86) PCT No.: PCT/US2011/049155
§ 371 (c)(1),
(2), (4) Date: Apr. 17, 2013

(87) PCT Pub. No.: WO2012/027575
PCT Pub. Date: Mar. 1, 2012

(65) Prior Publication Data
US 2013/0196065 A1    Aug. 1, 2013

Related U.S. Application Data

(60) Provisional application No. 61/377,692, filed on Aug. 27, 2010.

(51) Int. Cl.
C23C 16/40        (2006.01)
B05D 1/00        (2006.01)
(Continued)

(52) U.S. Cl.
CPC ............... B05D 1/60 (2013.01); C07F 11/00 (2013.01); C07F 17/00 (2013.01); C23C 16/405 (2013.01); C23C 16/45525 (2013.01)

(58) Field of Classification Search
USPC .......................................................... 556/57
See application file for complete search history.

(56) References Cited

U.S. PATENT DOCUMENTS

| | | |
|---|---|---|
| 5,064,686 A | 11/1991 | McGeary ....................... 427/124 |
| 6,698,728 B1 | 3/2004 | Ravetz et al. ............. 261/121.1 |

(Continued)

FOREIGN PATENT DOCUMENTS

| | | |
|---|---|---|
| CN | 101500989 A | 8/2009 |
| JP | 2005-534180 A | 11/2005 |

(Continued)

OTHER PUBLICATIONS

International Preliminary Report on Patentability dated Mar. 5, 2013 issued in PCT Application No. PCT/US2011/049155.

(Continued)

*Primary Examiner* — Joel Horning
(74) *Attorney, Agent, or Firm* — Harness, Dickey and Pierce, P.L.C.

(57) ABSTRACT

Molybdenum (IV) amide complexes are disclosed herein corresponding in structure to Formula (I): wherein: L is $-NR^1R^2$; $R^1$ and $R^2$ are $C_1$-$C_6$-alkyl or hydrogen; R is $C_1$-$C_6$-alkyl; and n is zero, 1, 2 or 3. Further, methods of forming $MoO_2$ films by atomic layer deposition (ALD) using Formula (I) complexes and $Mo[N(Me)(Et)]_4$ are disclosed herein.

1 Claim, 1 Drawing Sheet

(Formula I)

(51) Int. Cl.
*C07F 17/00* (2006.01)
*C23C 16/455* (2006.01)
*C07F 11/00* (2006.01)

(56) References Cited

U.S. PATENT DOCUMENTS

| | | | |
|---|---|---|---|
| 7,282,119 B2 | 10/2007 | Odedra et al. | 203/29 |
| 7,419,698 B2 | 9/2008 | Jones | 427/248.1 |
| 7,927,661 B2 | 4/2011 | Jones | 427/255.31 |
| 8,039,062 B2 | 10/2011 | Heys et al. | 427/585 |
| 8,221,852 B2 | 7/2012 | Heys et al. | 427/569 |
| 8,318,572 B1 * | 11/2012 | Shanker et al. | 438/381 |
| 2008/0003359 A1 | 1/2008 | Gordon et al. | |
| 2008/0282970 A1 | 11/2008 | Heys et al. | 117/104 |
| 2009/0074983 A1 | 3/2009 | Heys et al. | |
| 2010/0256406 A1 | 10/2010 | Kanjolia et al. | 556/136 |
| 2010/0261350 A1 | 10/2010 | Kanjolia et al. | 438/681 |
| 2011/0021803 A1 | 1/2011 | Jin et al. | 558/150 |
| 2011/0151227 A1 | 6/2011 | Chalker et al. | 428/220 |
| 2011/0165401 A1 | 7/2011 | Chalker et al. | 428/220 |
| 2011/0165780 A1 | 7/2011 | Kanjolia et al. | 438/785 |
| 2011/0184156 A1 | 7/2011 | Jones | 534/15 |
| 2012/0177845 A1 | 7/2012 | Odedra et al. | 427/569 |
| 2012/0178266 A1 | 7/2012 | Heys et al. | 438/785 |
| 2013/0041170 A1 | 2/2013 | Odedra et al. | 556/46 |
| 2013/0052368 A1 | 2/2013 | Rushworth et al. | |

FOREIGN PATENT DOCUMENTS

| | | | |
|---|---|---|---|
| TW | 200540291 | 12/2005 | C23C 16/34 |
| TW | 200912030 A | 3/2009 | |
| WO | WO-2004/010471 A2 | 1/2004 | |
| WO | WO 2008/002546 | 1/2008 | C07C 257/14 |
| WO | WO 2008/039960 | 4/2008 | C07F 7/10 |
| WO | WO 2009/117583 | 9/2009 | C07F 9/09 |
| WO | WO 2009/143452 | 11/2009 | C23C 16/40 |
| WO | WO 2009/143458 | 11/2009 | C23C 16/40 |
| WO | WO 2009/155507 | 12/2009 | C23C 16/18 |
| WO | WO 2009/155520 | 12/2009 | C23C 16/18 |
| WO | WO 2010/114386 | 10/2010 | C23C 16/40 |
| WO | WO 2012/027575 | 3/2012 | C07F 11/00 |
| WO | WO-2013112383 A1 | 8/2013 | |

OTHER PUBLICATIONS

George, S., et al. (1996) "Surface chemistry for atomic layer growth" Journal of Physical Chemistry, 100:13121-13131.

Green, J., et al. (1997) "Cyclopentadienyltris(dimethylamido)molybdenum: photoelectron spectroscopy, electron diffraction and theoretical calculations" Journal of the Chemical Society, pp. 3219-3224.

Herrmann, W., et al. (1995) "First amido-functionalized ansa-molybdenocene-type complexes" Journal of Organometallic Chemistry, 497:C4-C6.

Potter, R., et al. (2005) "Deposition of $HfO_2$, $Gd_2O_3$ and $PrO_x$ by liquid injection ALD techniques" Chemical Vapor Deposition, 11(3):159-169.

Yan, X., et al. (1997) "Synthesis of new amido, alkoxo and η-cyclopentadienyl derivatives of molybdenum" Journal of the Chemical Society, pp. 2091-2099.

International Search Report for PCT/US2011/049155 dated Jan. 25, 2012.

Chisholm, M.H., et al. (1976) "The molybdenum-molybdenum triple bond. 1. Hexakis(dimethylamido)dimolybdenum and some homologues: preparation, structure, and properties", *Journal of the American Chemical Society*, 98(15):4469-4476.

Office Action dated Mar. 3, 2015 issued in Taiwanese Patent Application No. 100130779—with English translation.

* cited by examiner

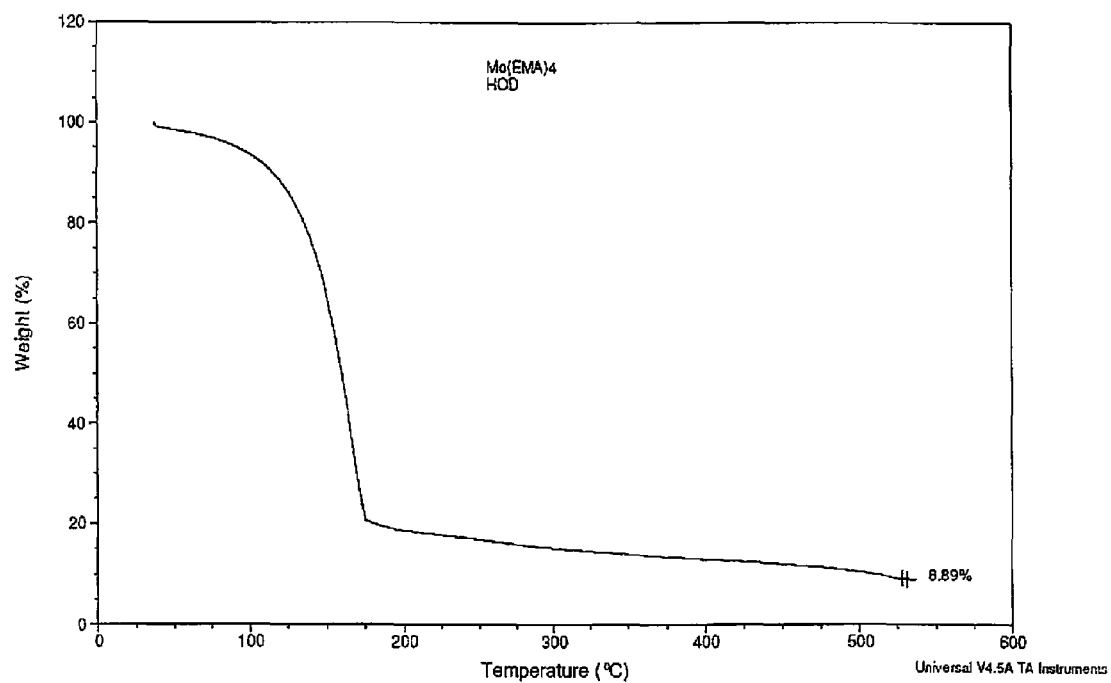

MOLYBDENUM (IV) AMIDE PRECURSORS AND USE THEREOF IN ATOMIC LAYER DEPOSITION

CROSS REFERENCE TO RELATED APPLICATIONS

This application claims priority to U.S. Patent Application Ser. No. 61/377,692 filed on 27 Aug. 2010, the entire disclosure of which is incorporated herein by reference.

FIELD OF THE INVENTION

The present invention relates to molybdenum (Mo) (IV) amide precursors and methods of preparing $MoO_2$ films by atomic layer deposition (ALD) using such precursors.

BACKGROUND OF THE INVENTION

ALD is a known method for the deposition of thin films. It is a self-limiting, sequential unique film growth technique based on surface reactions that can provide atomic layer control and deposit conformal thin films of materials provided by precursors onto substrates of varying compositions. In ALD, the precursors are separated during the reaction. The first precursor is passed over the substrate producing a monolayer on the substrate. Any excess unreacted precursor is pumped out of the reaction chamber. A second precursor is then passed over the substrate and reacts with the first precursor, forming a monolayer of film on the substrate surface. This cycle is repeated to create a film of desired thickness.

ALD processes have applications in nanotechnology and fabrication of semiconductor devices such as capacitor electrodes, gate electrodes, adhesive diffusion barriers and integrated circuits. Further, dielectric thin films having high dielectric constants (permittivities) are necessary in many sub-areas of microelectronics and optelectronics. The continual decrease in the size of microelectronics components has increased the need for the use of such dielectric films.

Green, J., et al. report the synthesis and isolation of the Mo complex, $Mo(C_5H_5)(NMe_2)_3$. *J. Chem. Soc., Dalton Trans.*, 1997, Pages 3219-3224.

U.S. Pat. No. 5,064,686 reports a Mo (IV) complex for use in chemical vapor deposition (CVD). $Mo[N(Me)(Me)]_4$ was attempted in CVD. However, issues with thermal stability were noted in CVD and it has been found that although this precursor is similar in structure, it is not suitable for depositing a $MoO_2$ layer.

Further, it was found that $Mo(NtBu)_2(NMe_2)_2$ did not work well for forming $MoO_2$ films by ALD because it formed $MoO_3$ films which is unsuitable for DRAM. Therefore a need exists to discover new Mo precursors which are capable of depositing $MoO_2$ films by ALD, which have improved thermal stability, higher volatility or increased deposition rates.

SUMMARY OF THE INVENTION

In one embodiment, a complex corresponding in structure to Formula I

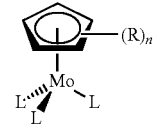

(Formula I)

is provided wherein L is $-NR^1R^2$; $R^1$ and $R^2$ are $C_1$-$C_6$-alkyl or hydrogen; R is $C_1$-$C_6$-alkyl; and n is zero, 1, 2 or 3.

In another embodiment, a method of forming a $MoO_2$ film by ALD is provided. The method comprises delivering at least one precursor to a substrate, wherein the at least one precursor corresponds in structure to Formula I above.

In another embodiment, the complex $Mo[N(Me)(Et)]_4$ is provided and its use in ALD to form $MoO_2$ films.

Other embodiments, including particular aspects of the embodiments summarized above, will be evident from the detailed description that follows.

BRIEF DESCRIPTION OF THE DRAWINGS

FIG. 1 is a graphical representation of thermogravimetric analysis (TGA) data demonstrating mg vs. temperature/time of $Mo[N(Me)(Et)]_4$.

DETAILED DESCRIPTION OF THE INVENTION

In various aspects of the invention, Mo (IV) amide precursors are provided and methods of use thereof are provided to form $MoO_2$ films by ALD.

In one embodiment, the methods of the invention can be used to create or grow Mo-containing thin films which display high dielectric constants. A dielectric thin film as used herein refers to a thin film having a high permittivity.

As used herein, the term "precursor" refers to an organometallic molecule, complex and/or compound which is delivered to a substrate for deposition to form a thin film by ALD.

The term "Cp" refers to a cyclopentadienyl ($C_5H_5$) ligand which is bound to a transition metal. As used herein, all five carbon atoms of the Cp ligand are bound to the metal center in $\eta^5$-coordination by π bonding, therefore the precursors of the invention are π complexes.

The term "alkyl" refers to a saturated hydrocarbon chain of 1 to about 6 carbon atoms in length, such as, but not limited to, methyl, ethyl, propyl and butyl. The alkyl group may be straight-chain or branched-chain. For example, as used herein, propyl encompasses both n-propyl and iso-propyl; butyl encompasses n-butyl, sec-butyl, iso-butyl and tert-butyl. Further, as used herein, "Me" refers to methyl, and "Et" refers to ethyl.

The term "amino" herein refers to an optionally substituted monovalent nitrogen atom (i.e., $-NR^1R^2$, where $R^1$ and $R^2$ can be the same or different). Examples of amino groups encompassed by the invention include but are not limited to

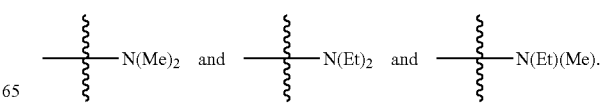

Further, the nitrogen atom of this amino group is covalently bonded to the metal center which together may be referred to as an "amide" group (i.e.

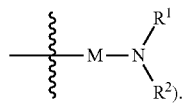

This can be further referred to as an "ammono" group or inorganic amide.

In a first embodiment, a "pianostool" complex corresponding in structure to Formula I

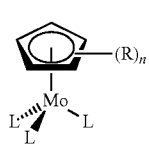

(Formula I)

is provided wherein: L is —NR$^1$R$^2$; R$^1$ and R$^2$ are independently C$_1$-C$_6$-alkyl or hydrogen; R is C$_1$-C$_6$-alkyl; and n is zero, 1, 2 or 3.

R$^1$ and R$^2$ can be the same or different. In a particular embodiment, both R$^1$ and R$^2$ are methyl. In another particular embodiment, R$^1$ is methyl and R$^2$ is ethyl.

In a further embodiment, when n is zero, R$^1$ and R$^2$ are different from each other.

In one embodiment, R$^1$ and R$^2$ are independently methyl, ethyl or propyl; R is methyl, ethyl or propyl; and n is zero, 1 or 2.

In another embodiment, R$^1$ and R$^2$ are the same; R is methyl; n is zero, 1 or 2.

In another embodiment, R$^1$ is methyl and R$^2$ is ethyl; R is methyl; and n is zero, 1 or 2.

Examples of complexes corresponding in structure to Formula I is
(cyclopentadienyl)Mo(NMe$_2$)$_3$;
(methylcyclopentadienyl)Mo(NMe$_2$)$_3$;
(ethylcyclopentadienyl)Mo(NMe$_2$)$_3$;
(propylcyclopentadienyl)Mo(NMe$_2$)$_3$;
(methylcyclopentadienyl)Mo(NEt$_2$)$_3$;
(ethylcyclopentadienyl)Mo(NEt$_2$)$_3$;
(propylcyclopentadienyl)MoNEt$_2$)$_3$;
(cyclopentadienyl)Mo(NMeEt)$_3$;
(methylcyclopentadienyl)Mo(NMeEt)$_3$;
(ethylcyclopentadienyl)Mo(NMeEt)$_3$; and
(propylcyclopentadienyl)Mo(NMeEt)$_3$.

In another embodiment, the cyclopentadienyl ring on the Mo (IV) amide complex is replaced with another amide group to form a tetrakisamide: Mo[N(Me)(Et)]$_4$.

The complexes according to Formula I and Mo[N(Me)(Et)]$_4$ are used as precursors to form MoO$_2$ films by ALD. The precursors disclosed herein may be delivered for deposition to a substrate in pulses alternating with pulses of an appropriate oxygen source, such as H$_2$O, H$_2$O$_2$, O$_2$, ozone, iPrOH, tBuOH or N$_2$O.

In one embodiment a MoO$_2$ film can be formed by delivering for deposition at least one precursor according to Formula I, independently or in combination with a co-reactant. Examples of such co-reactants include, but are not limited to hydrogen, hydrogen plasma, oxygen, air, water, H$_2$O$_2$, ammonia, hydrazines, alkylhydrazines, boranes, silanes, ozone or any combination thereof.

A variety of substrates can be used in the methods of the present invention. For example, the precursors according to Formula I or Mo[N(Me)(Et)]$_4$ may be delivered for deposition on substrates such as, but not limited to, silicon, silicon oxide, silicon nitride, tantalum, tantalum nitride, or copper.

The ALD methods of the invention encompass various types of ALD processes. For example, in one embodiment conventional ALD is used to form a metal-containing film of the invention. For conventional and/or pulsed injection ALD process see for example, George S. M., et. al. *J. Phys. Chem.* 1996. 100:13121-13131.

In another embodiment, liquid injection ALD is used to form a metal-containing film, wherein a liquid precursor is delivered to the reaction chamber by direct liquid injection as opposed to vapor draw by a bubbler (conventional). For liquid injection ALD process see, for example, Potter R. J., et. al. *Chem. Vap. Deposition.* 2005. 11(3):159.

Examples of liquid injection ALD growth conditions include, but are not limited to:
(1) Substrate temperature: 160-300° C. on Si(100)
(2) Evaporator temperature range: about 120-200° C.
(3) Reactor pressure range: about 2-50 mbar
(4) Solvent: toluene, or any solvent mentioned above
(5) Solution concentration Range: about 0.05 to 2 M
(6) Injection rate range: about 1-10 µl pulse$^{-1}$ (4 pulses cycle$^{-1}$)
(7) Inert gas flow rate: about 50-500 cm$^3$ min$^{-1}$
(8) Pulse sequence (sec.) (precursor/purge/H$_2$O/purge): will vary according to chamber size.
(9) Number of cycles: will vary according to desired film thickness.

The precursor may be dissolved in an appropriate hydrocarbon or amine solvent. Appropriate hydrocarbon solvents include, but are not limited to aliphatic hydrocarbons, such as hexane, heptane and nonane; aromatic hydrocarbons, such as toluene and xylene; aliphatic and cyclic ethers, such as diglyme, triglyme and tetraglyme. Examples of appropriate amine solvents include, without limitation, octylamine and N,N-dimethyldodecylamine. For example, the precursor may be dissolved in toluene to yield a 0.05 to 1M solution.

In another embodiment, at least one precursor corresponding in structure to Formula I and/or Mo[N(Me)(Et)]$_4$ may be delivered "neat" (undiluted by a carrier gas) to the substrate.

In another embodiment, photo-assisted ALD is used to form a metal-containing film. For photo-assisted ALD processes see, for example, U.S. Pat. No. 4,581,249.

In another embodiment, both liquid injection and photo-assisted ALD may be used to form a metal-containing film using at least one precursor corresponding in structure to Formula I and/or Mo[N(Me)(Et)]$_4$.

In another embodiment, plasma-assisted ALD may be used to form a metal-containing film using at least one precursor corresponding in structure to Formula I and/or Mo[N(Me) (Et)]$_4$.

Thus, the organometallic precursors corresponding in structure to Formula I and Mo[N(Me)(Et)]$_4$ utilized in these methods may be liquid, solid, or gaseous. Particularly, the precursors are liquid at ambient temperatures with high vapor pressure for consistent transport of the vapor to the process chamber.

ALD relies substantially on chemical reactivity and not thermal decomposition. Therefore, there are fundamental differences in the characteristics desirable for a suitable precursor. The precursor must be thermally stable at the temperatures employed and should be sufficiently volatile to allow deposition onto the substrate. Further, when depositing a metal oxide film, a fast and complete chemical reaction is necessary between the metal precursor and the oxide source. However the reaction should only take place at the substrate surface so as not to damage the underlying structure and by-products, such as carbon and hydrogen, should be removed readily from the surface.

It has been discovered that variation of the substitution of the Cp ring and three identical ligands attached to the metal center demonstrates useful and improved properties for ALD processes. For example, the precursors of Formula I provide an increased ability to deposit $MoO_2$ films by ALD at growth rates approaching that for simple metal amides but can operate at higher temperatures due to increased thermal stability which leads to improved product quality. Moreover, the use of Mo(IV) amide pianostool-type complexes enhances ALD performance by polarizing the molecule to allow reaction with the surface which can be saturative to self-limit film growth for excellent conformal control.

In particular embodiments, the methods of the invention are utilized for applications such as dynamic random access memory (DRAM) and complementary metal oxide semiconductor (CMOS) for memory and logic applications, on substrates such as silicon chips.

In a further embodiment, a method is provided for forming a "mixed" metal film by ALD. The term "mixed" metal film as used herein is to indicate that at least two different metals comprise the film.

In one embodiment, a mixed-metal film is formed by ALD by delivering for deposition at least one precursor according to Formula I and/or $Mo[N(Me)(Et)]_4$ and at least one co-precursor having a different metal center. For example, at least one Mo precursor according to Formula I and/or $Mo[N(Me)(Et)]_4$ and at least one appropriate co-precursor, such as a lead, titanium, strontium and/or barium precursor may be delivered for deposition to a substrate to create a mixed-metal film.

A thin film created by a method of the invention can have a permittivity of between 10 and 250, preferably at least 25 to 40 and more preferably at least 40 to 100. Further, an ultra high permittivity can be considered to be a value higher than 100. It is understood by one of ordinary skill in the art that the resulting permittivity of the film depends on a number of factors, such as the metal(s) used for deposition, the thickness of the film created, the parameters and substrate employed during growth and subsequent processing.

EXAMPLES

The following examples are merely illustrative, and do not limit this disclosure in any way. All manipulations were carried out in an inert atmosphere using a glove box and Schlenk line techniques. NMR analysis was carried out using a Bruker 250 MHz machine.

Example 1

Synthesis of $Mo(NMeEt)_4$

Lithium N-ethyl,methylamide was prepared using standard techniques from $^n$BuLi and HNEtMe. To $^n$BuLi (680 ml, 1.6M in hexanes, cooled to 0° C. with ice bath) was added drop-wise over a period of 4 hours N-ethylmethylamine (65.6 g, 1.1 moles). The mixture was allowed to warm to room temperature once all the amine had been added and was then stirred overnight. To this was added THF (250 ml) and the mixture stirred for 1 hour and then cooled to 0° C. in an ice bath. To this mixture was added $MoCl_5$ (50.2 g, 0.18 moles, added in small portions of ~12 g over a period of 8 hrs due to large exotherm and spitting of mixture). The dark brown (almost black) reaction mixture was allowed to warm to room temperature once all the $MoCl_5$ had been added and was then refluxed for 1 hour. The mixture was cooled and then stirred overnight. The mixture was allowed to settle (LiCl) and filtered using standard technique. Solvent was stripped from the reaction mixture and then the purple liquid sublimed/distilled out of the reaction mixture to yield a purple liquid.

Distillation conditions: pressure in the range $3.5 \times 10^{-2}$ Torr and oil bath temperature 100-110° C.

| $Mo(NEtMe)_4$ NMR | |
|---|---|
| δ, ppm - (integrations) | Assignment |
| 1.17 (12 H) | Ethyl $CH_3$, i.e. $NCH_2\mathbf{CH_3}$ |
| 3.22 (8 H) | Ethyl $CH_2$, i.e. $N\mathbf{CH_2}CH_3$ |
| 3.49 (12 H) | Methyl on nitrogen, i.e. $N\mathbf{CH_3}$ |

FIG. 1 displays TGA data for $Mo(NMeEt)_4$.

Example 2

Synthesis of $[Mo(MeCp)(NEtMe)_3]$

To a dark purple toluene solution (60 ml) of $Mo(NEtMe)_4$ (prepared above, 3.3 g, 0.01 moles) cooled to 0° C. in an ice bath was added freshly cracked MeCpH (4 g, 0.05 moles, added via syringe). No immediate colour change was observed and so the mixture was allowed to stir at room temperature for 2 hrs. Again no colour changes were observed and so the mixture was refluxed for 3 hrs to produce a dark green solution. The toluene was stripped form the reaction mixture to yield a dark green liquid.

| $Mo(^{Me}Cp)(NEtMe)_3$ | |
|---|---|
| 1.00, (9 H) | Ethyl $CH_3$, i.e. $CH_2\mathbf{CH_3}$ |
| 1.60, (3 H) | Methyl group on Cp ring, i.e. $\mathbf{Me}Cp$ |
| 2.95, (9 H) | Methyl on nitrogen, i.e. $N\mathbf{CH_3}$ |
| 3.15, (6 H) | Ethyl $CH_2$, i.e. $N\mathbf{CH_2}CH_3$ |
| 4.95 (2 H) | Cp ring Hydrogen |
| 5.15, (2 H) | Cp ring Hydrogen |

Example 3

ALD using $[Mo(MeCp)(NEtMe)_3]$ $MoO_2$ films are deposited in a custom-built ALD reactor. $Mo(MeCp)(NEtMe)_3$ and ozone are used as precursors. The $MoO_2$ films are deposited on silicon wafer substrates. Prior to deposition, the wafer substrates are prepared by dicing the wafer (1 inch×½ inch), and 1% HF polish.

The growth temperature is 200-350° C. The growth pressure is 0.5-1.5 Torr. The reactor is continuously purged with 30 sccm of dry nitrogen. All the computer controlled valves in the reactor are the air operated ALD VCR valves from Cajon.

Ozone is purged in excess. The molybdenum is stored in a stainless steel ampoule. Attached directly to the ampoule is an ALD valve. The output of this ALD valve is Tee'd with another ALD valve used for nitrogen injection. The Tee outlet leg is connected to a 500 cm$^3$ stainless steel reservoir. The outlet of the reservoir is attached to a third ALD valve, called the inject valve, whose outlet goes directly to the reactor. Nitrogen injection is used to build up the total pressure behind the molybdenum inject valve so that the pressure is higher than the reactor growth pressure. The injected nitrogen is accomplished using a 30 micron pin hole VCR gasket. All of the valves and ampoule are placed into an oven-like enclosure that allows the ampoule, valves, and tubing to be heated uniformly to 50° C. to 250° C.

During the ALD growth operation, the valves are sequenced in the following manner. The molybdenum precursor is introduced to the activated silicon surface. A nitrogen purge then takes place which includes evacuation to remove surplus reactant molecules not attached to the surface. Ozone is then introduced followed by an additional purge with nitrogen. The ozone is then injected to start the ALD cycle all over again.

The total amount of cycles is typically 300.

All patents and publications cited herein are incorporated by reference into this application in their entirety.

The words "comprise", "comprises", and "comprising" are to be interpreted inclusively rather than exclusively.

What is claimed is:

1. A method of forming a $MoO_2$ film by atomic layer deposition, the method comprising delivering $Mo[N(Me)(Et)]_4$ to a substrate.

* * * * *